United States Patent
Govea et al.

(10) Patent No.: US 9,833,611 B2
(45) Date of Patent: Dec. 5, 2017

(54) SYSTEMS AND METHODS FOR MAKING AND USING IMPROVED CONTACT ARRAYS FOR ELECTRICAL STIMULATION SYSTEMS

(71) Applicant: Boston Scientific Neuromodulation Corporation, Valencia, CA (US)

(72) Inventors: Michael X. Govea, Glendale, CA (US); Joshua Dale Howard, Sacramento, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 15/091,396

(22) Filed: Apr. 5, 2016

(65) Prior Publication Data

US 2016/0296745 A1 Oct. 13, 2016

Related U.S. Application Data

(60) Provisional application No. 62/146,017, filed on Apr. 10, 2015.

(51) Int. Cl.
*A61N 1/05* (2006.01)
*A61N 1/375* (2006.01)
*A61N 1/36* (2006.01)

(52) U.S. Cl.
CPC .............. *A61N 1/05* (2013.01); *A61N 1/36* (2013.01); *A61N 1/3752* (2013.01); *A61N 1/0529* (2013.01); *A61N 1/0551* (2013.01)

(58) Field of Classification Search
CPC .......... A61N 1/05; A61N 1/36; A61N 1/3752; A61N 1/0529; A61N 1/0551
See application file for complete search history.

(56) References Cited

U.S. PATENT DOCUMENTS 4,602,624 A 7/1986 Naples et al.
4,630,611 A 12/1986 King
(Continued)

FOREIGN PATENT DOCUMENTS

EP 0580928 A1 2/1994
EP 0650694 B1 7/1998
(Continued)

OTHER PUBLICATIONS

U.S. Appl. No. 62/113,291, filed Feb. 6, 2015.
International Search Report and Written Opinion for PCT/US2016/026044 dated Jun. 22, 2016.

*Primary Examiner* — Paula J Stice
(74) *Attorney, Agent, or Firm* — Lowe Graham Jones PLLC; Bruce E. Black

(57) ABSTRACT

An electrical stimulation lead or lead extension includes a body having an outer surface, a proximal end, a proximal portion, at least one distal portion, an outer surface, a perimeter, and a longitudinal length, the body defining an alignment slit extending distally from the proximal end of the body and splitting the proximal portion of the body into two transversely space-apart sections; first contacts disposed along the distal portion of the body; segmented second contacts disposed along the proximal portion of the body, where each segmented second contact extends around less than the entire perimeter of the body and is separated from all other segmented second contacts by portions of the body or the alignment slit; and conductors electrically coupling the first contacts to the second contacts.

20 Claims, 13 Drawing Sheets

(56) References Cited

U.S. PATENT DOCUMENTS

| | | |
|---|---|---|
| 4,744,370 A | 5/1988 | Harris |
| 5,000,194 A | 3/1991 | van den Honert et al. |
| 5,135,001 A | 8/1992 | Sinofsky et al. |
| 5,374,285 A | 12/1994 | Vaiani et al. |
| 5,458,629 A | 10/1995 | Baudino et al. |
| 5,522,874 A | 6/1996 | Gates |
| 5,711,316 A | 1/1998 | Elsberry et al. |
| 5,713,922 A | 2/1998 | King |
| 5,800,350 A | 9/1998 | Coppleson et al. |
| 5,843,148 A | 12/1998 | Gijsbers et al. |
| 5,938,688 A | 8/1999 | Schiff |
| 5,987,361 A | 11/1999 | Mortimer |
| 6,018,684 A | 1/2000 | Bartig et al. |
| 6,134,478 A | 10/2000 | Spehr |
| 6,161,047 A | 12/2000 | King et al. |
| 6,167,311 A | 12/2000 | Rezai |
| 6,181,969 B1 | 1/2001 | Gord |
| 6,322,559 B1 | 11/2001 | Daulton et al. |
| 6,510,347 B2 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,609,029 B1 | 8/2003 | Mann et al. |
| 6,609,032 B1 | 8/2003 | Woods et al. |
| 6,678,564 B2 | 1/2004 | Ketterl et al. |
| 6,741,892 B1 | 5/2004 | Meadows et al. |
| 6,757,970 B1 | 7/2004 | Kuzma et al. |
| 7,027,852 B2 | 4/2006 | Helland |
| 7,047,084 B2 | 5/2006 | Erickson et al. |
| 7,203,548 B2 | 4/2007 | Whitehurst et al. |
| 7,244,150 B1 | 7/2007 | Brase et al. |
| 7,292,890 B2 | 11/2007 | Whitehurst et al. |
| 7,437,193 B2 | 10/2008 | Parramon et al. |
| 7,450,997 B1 | 11/2008 | Pianca et al. |
| 7,489,971 B1 | 2/2009 | Franz |
| 7,668,601 B2 | 2/2010 | Hegland et al. |
| 7,672,734 B2 | 3/2010 | Anderson et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,809,446 B2 | 10/2010 | Meadows |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,175,710 B2 | 5/2012 | He |
| 8,224,450 B2 | 7/2012 | Brase |
| 8,225,504 B2 | 7/2012 | Dye et al. |
| 8,271,094 B1 | 9/2012 | Moffitt et al. |
| 8,295,944 B2 | 10/2012 | Howard et al. |
| 8,321,025 B2 | 11/2012 | Bedenbaugh |
| 8,359,107 B2 | 1/2013 | Pianca et al. |
| 8,364,278 B2 | 1/2013 | Pianca et al. |
| 8,391,985 B2 | 3/2013 | McDonald |
| 8,583,237 B2 | 11/2013 | Bedenbaugh |
| 8,688,235 B1 | 4/2014 | Pianca et al. |
| 2001/0023368 A1 | 9/2001 | Black et al. |
| 2002/0156513 A1 | 10/2002 | Borkan |
| 2002/0183817 A1 | 12/2002 | Van Venrooij et al. |
| 2005/0015130 A1 | 1/2005 | Gill |
| 2005/0038489 A1 | 2/2005 | Grill |
| 2005/0171587 A1 | 8/2005 | Daglow et al. |
| 2006/0025841 A1 | 2/2006 | McIntyre |
| 2006/0247697 A1 | 11/2006 | Sharma et al. |
| 2007/0150036 A1 | 6/2007 | Anderson |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0215125 A1 | 9/2008 | Farah et al. |
| 2008/0255647 A1 | 10/2008 | Jensen et al. |
| 2009/0054941 A1 | 2/2009 | Eggen et al. |
| 2009/0187222 A1 | 7/2009 | Barker |
| 2009/0204192 A1 | 8/2009 | Carlton et al. |
| 2009/0276021 A1 | 11/2009 | Meadows et al. |
| 2010/0030298 A1 | 2/2010 | Martens et al. |
| 2010/0036468 A1 | 2/2010 | Decre et al. |
| 2010/0057176 A1* | 3/2010 | Barker ............... A61N 1/0551 607/117 |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca |
| 2011/0082516 A1* | 4/2011 | Kast ................... A61N 1/05 607/46 |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0245903 A1 | 10/2011 | Schulte et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203302 A1 | 8/2012 | Moffit et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0259386 A1 | 10/2012 | DeRohan et al. |
| 2012/0316615 A1 | 12/2012 | DiGiore et al. |
| 2013/0105071 A1 | 5/2013 | DiGiore et al. |
| 2013/0109254 A1 | 5/2013 | Klardie et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0180375 A1 | 6/2014 | Pianca et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0151113 A1 | 6/2015 | Govea et al. |
| 2015/0360023 A1 | 12/2015 | Howard et al. |
| 2015/0374978 A1 | 12/2015 | Howard et al. |

(56) References Cited

U.S. PATENT DOCUMENTS

2016/0059019 A1    3/2016    Malinowski et al.
2016/0129242 A1    5/2016    Malinowski
2016/0129265 A1    5/2016    Malinowski

FOREIGN PATENT DOCUMENTS

| EP | 0832667 B1 | 2/2004 |
|---|---|---|
| EP | 1181947 B1 | 1/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2009/148939 | 12/2009 |
| WO | 2013162775 A2 | 10/2013 |
| WO | 2014018092 A1 | 1/2014 |

\* cited by examiner

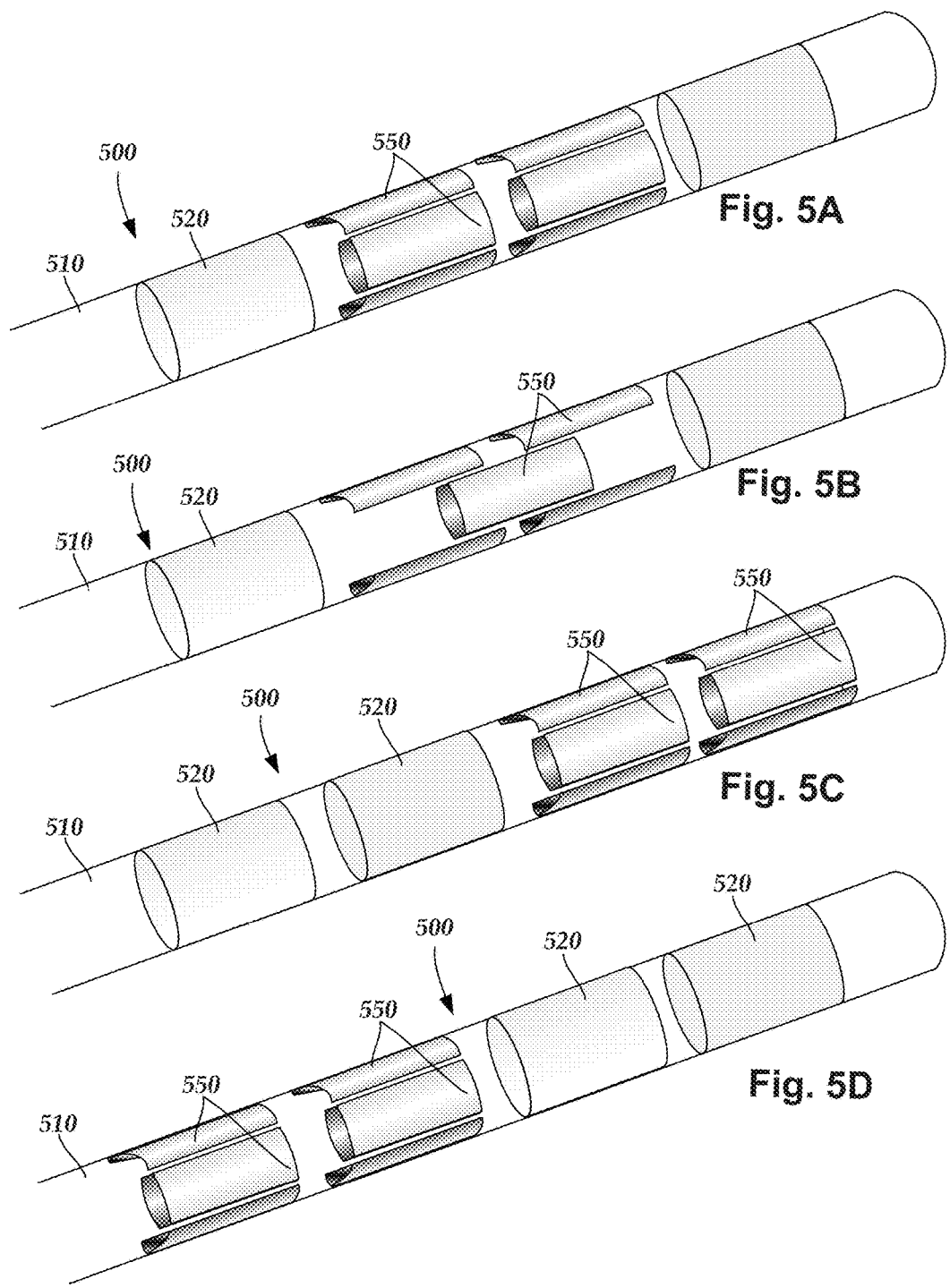

SYSTEMS AND METHODS FOR MAKING AND USING IMPROVED CONTACT ARRAYS FOR ELECTRICAL STIMULATION SYSTEMS

CROSS-REFERENCE TO RELATED APPLICATIONS

This application claims the benefit under 35 U.S.C. §119(e) of U.S. Provisional Patent Application Ser. No. 62/146,017, filed Apr. 10, 2015, which is incorporated herein by reference.

FIELD

The present invention is directed to the area of implantable electrical stimulation systems and methods of making and using the systems. The present invention is also directed to implantable electrical stimulation systems having elongated members with improved contact arrays, as well as methods of making and using the elongated devices, contact arrays, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an electrical stimulation lead or lead extension that includes a body having an outer surface, a proximal end, a proximal portion, at least one distal portion, an outer surface, a perimeter, and a longitudinal length, the body defining an alignment slit extending distally from the proximal end of the body and splitting the proximal portion of the body into two transversely space-apart sections; first contacts disposed along the distal portion of the body; segmented second contacts disposed along the proximal portion of the body. Where each segmented second contact extends around less than the entire perimeter of the body and is separated from all other segmented second contacts by portions of the body or the alignment slit; and conductors electrically coupling the first contacts to the second contacts.

In at least some embodiments, the segmented second contacts are arranged in sets of segmented second contacts, where each set of segmented second contacts includes at least two of the segmented second contacts disposed in a circumferential arrangement at a same longitudinal position of the lead. In at least some embodiments, the alignment slit extends between at least two of the segmented second contacts of each of the sets of segmented second contacts. In at least some embodiments, each of the sets of segmented second contacts contains exactly two segmented second contacts.

In at least some embodiments, the electrical stimulation lead or lead extension further includes a retention sleeve disposed distal of all of the segmented second contacts. In at least some embodiments, the alignment slit separates the retention sleeve into two laterally spaced-apart pieces. In at least some embodiments, the alignment slit terminates proximal to the retention sleeve.

In at least some embodiments, the alignment slit separates the proximal portion of the body into two branches, where each branch further defines a bendable portion distal to all of the segmented second contacts and the bendable portions of the two branches allow the branches to be sufficiently separated so that the branches can be inserted into different connectors. In at least some embodiments, the first and second branches each have a hemispherical lateral cross-sectional shape.

In at least some embodiments, the first contacts are electrodes and the segmented second contacts are segmented terminals and the electrical stimulation lead or lead extension is an electrical stimulation lead. In at least some embodiments, the first contacts are connector contacts and the segmented second contacts are segmented terminals and the electrical stimulation lead or lead extension is a lead extension.

Another embodiment is an electrical stimulation system that includes any of the electrical stimulation leads or lead extensions described above; and a first connector defining a connector lumen to receive at least a portion of the proximal end of the electrical stimulation lead or lead extension. The first connector includes segmented connector contacts disposed along the connector lumen.

In at least some embodiments, the electrical stimulation system further includes a control module that includes the connector, a housing, and an electrical subassembly disposed in the housing and electrical coupled to the connector contacts of the connector. In at least some embodiments, the electrical stimulation system further includes a lead extension that includes the connector.

In at least some embodiments, the connector contacts of the first connector are arranged in sets of segmented connector contacts, where each set of segmented connector contacts includes at least two of the segmented connector contacts disposed in a circumferential arrangement at a same longitudinal position along the connector lumen. In at least some embodiments, the connector further includes a connector housing containing the connector lumen and defining an opening into the connector lumen, and an alignment structure extending across the connector lumen and configured and arranged to mate with the alignment slit of the electrical stimulation lead or lead extension.

In at least some embodiments, the electrical stimulation system further includes a second connector defining a connector lumen to receive the proximal end of the electrical stimulation lead or lead extension, where the second connector includes a plurality of segmented connector contacts disposed along the connector lumen. The electrical stimulation lead or lead extension is configured and arranged so that the alignment slit separates the proximal portion of the body into a first branch and a second branch, where each of the first and second branched further defines a bendable portion distal to all of the segmented second contacts, and the bendable portions of the first and second branches allow the first and second branches to be sufficiently separated so that the first and second branches can be separately inserted into the first and second connectors, respectively. In at least some embodiments, the first and second branches each have a hemispherical lateral cross-sectional shape.

A further embodiment is a control module for an electrical stimulation system that includes a housing; an electrical subassembly disposed in the housing; and a connector disposed in the housing, defining at least one connector lumen, and including conductive contacts disposed around the at least one connector lumen and an alignment structure extending across the connector lumen and configured and arranged to mate with an alignment slit of an electrical stimulation lead or lead extension.

Yet another embodiment is a control module for an electrical stimulation system that includes a housing; an electrical subassembly disposed in the housing; and at least two connectors disposed in the housing, each connector defining a connector lumen, and including conductive contacts disposed around the connector lumen. The connector lumen has a hemispherical lateral cross-sectional shape and is configured and arranged to receive a proximal portion of a lead or lead extension.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 5A is a schematic perspective view of one embodiment of a distal end of a lead containing segmented electrodes, according to the invention;

FIG. 5B is a schematic perspective view of a second embodiment of a distal end of a lead containing segmented electrodes, according to the invention;

FIG. 5C is a schematic perspective view of a third embodiment of a distal end of a lead containing segmented electrodes, according to the invention;

FIG. 5D is a schematic perspective view of a fourth embodiment of a distal end of a lead containing segmented electrodes, according to the invention;

DETAILED DESCRIPTION

The present invention is directed to the area of implantable electrical stimulation systems and methods of making and using the systems. The present invention is also directed to implantable electrical stimulation systems having elongated members with improved contact arrays, as well as methods of making and using the elongated devices, contact arrays, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead.

Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference.

Figure 1:
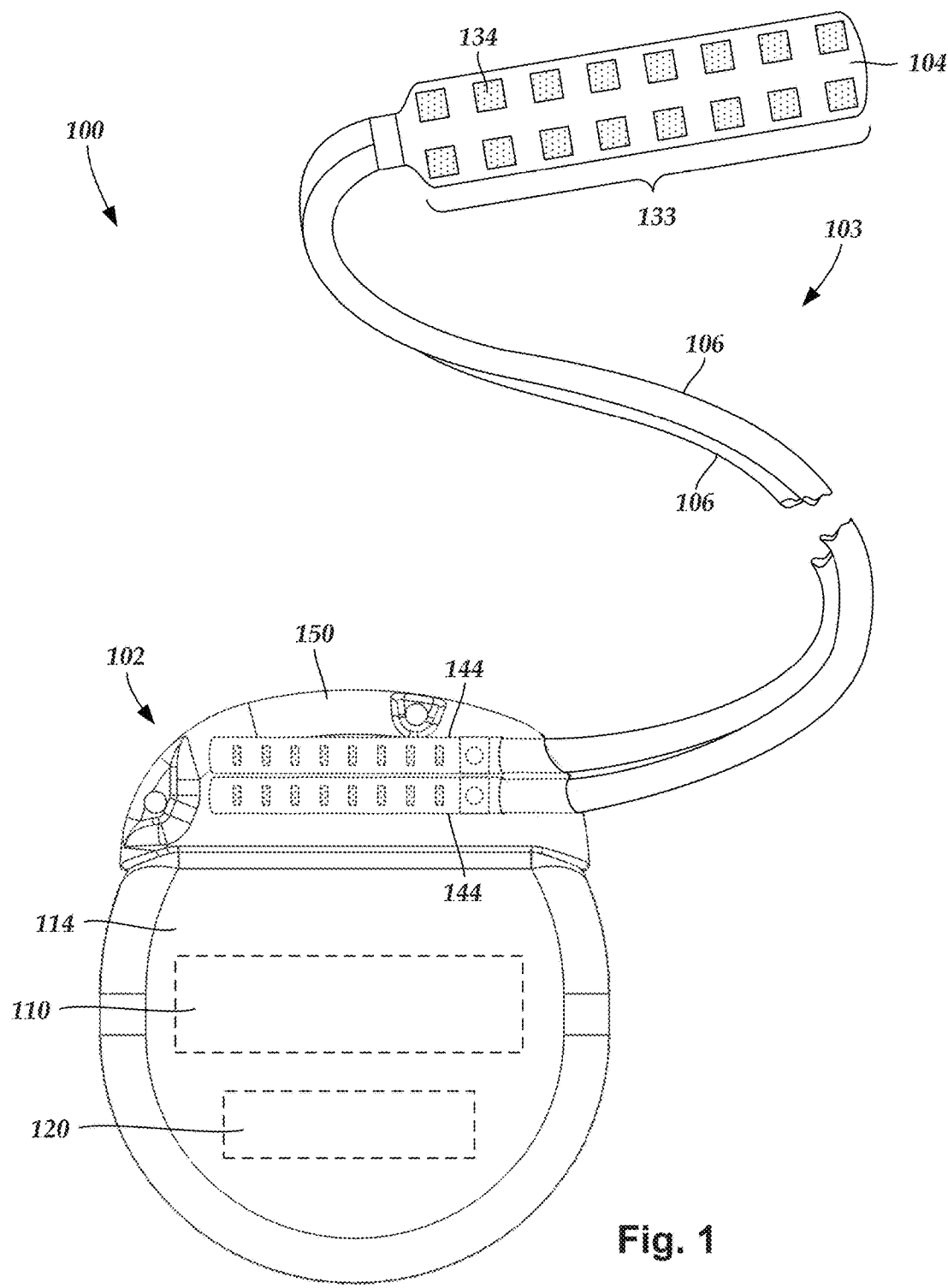
FIG. 1 is a schematic view of one embodiment of an implantable medical device that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102 and a lead 103. The lead 103 including a paddle body 104 and one or more lead bodies 106 coupling the control module 102 to the paddle body 104. The paddle body 104 and the one or more lead bodies 106 form the lead 103. The paddle body 104 typically includes a plurality of electrodes 134 that form an array of electrodes 133. The control module 102 typically includes an electronic subassembly 110 and an optional power source 120 disposed in a sealed housing 114. In FIG. 1, two lead bodies 106 are shown coupled to the control module 102.

Figure 3A:
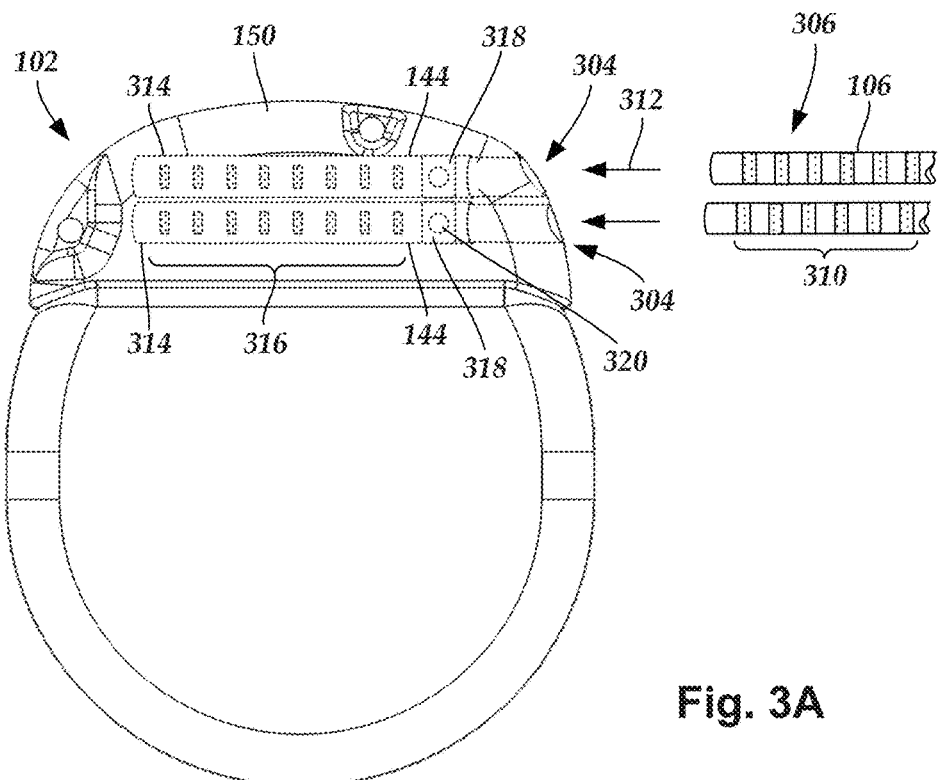
FIG. 3A is a schematic view of one embodiment of a plurality of connectors disposed in the control module of FIG. 1, the connectors configured and arranged to receive the proximal portions of the lead bodies of FIG. 1, according to the invention.

The control module 102 typically includes one or more connectors 144 into which the proximal end of the one or more lead bodies 106 can be plugged to make an electrical connection via connector contacts (e.g., 316 in FIG. 3A) disposed in the connector 144 and terminals 310 in FIG. 3A) on each of the one or more lead bodies 106. The connector contacts are coupled to the electronic subassembly 110 and the terminals are coupled to the electrodes 134. In FIG. 1, two connectors 144 are shown.

The one or more connectors 144 may be disposed in a header 150. The header 150 provides a protective covering over the one or more connectors 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
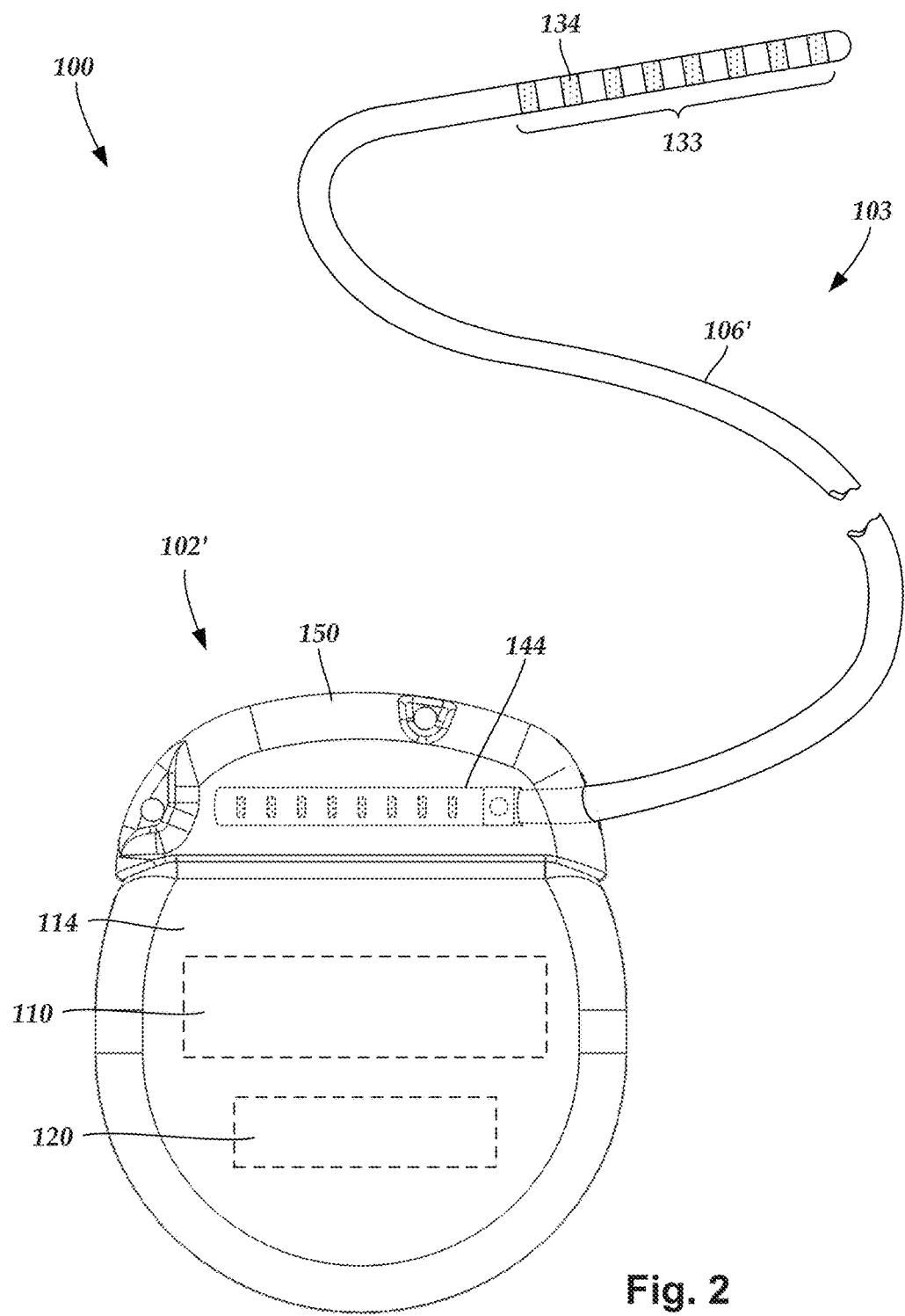
FIG. 2 is a schematic view of another embodiment of an implantable medical device that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead 103, as illustrated in FIG. 2. The percutaneous lead may be isodiametric along the length of the lead body 106". The lead body 106' can be coupled with a control module 102' with a single connector 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, anonconductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead 103 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connectors (e.g., 144 in FIG. 1) disposed on, for example, the control module 102 (or to other devices, such as conductive contacts on a lead extension, an operating room cable, a splitter, an adaptor, or the like).

Conductive wires, such as conductors (e.g, 912 in FIG. 9A), extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connectors 144 disposed on the control module 102. The control module 102 can include any suitable number of connectors 144 including, for example, two three, four, five, six, seven, eight, or more connectors 144. It will be understood that other numbers of connectors 144 may be used instead. In FIG. 1, each of the two lead bodies 106 includes eight terminals that are shown coupled with eight conductive contacts disposed in a different one of two different connectors 144.

Figure 3B:
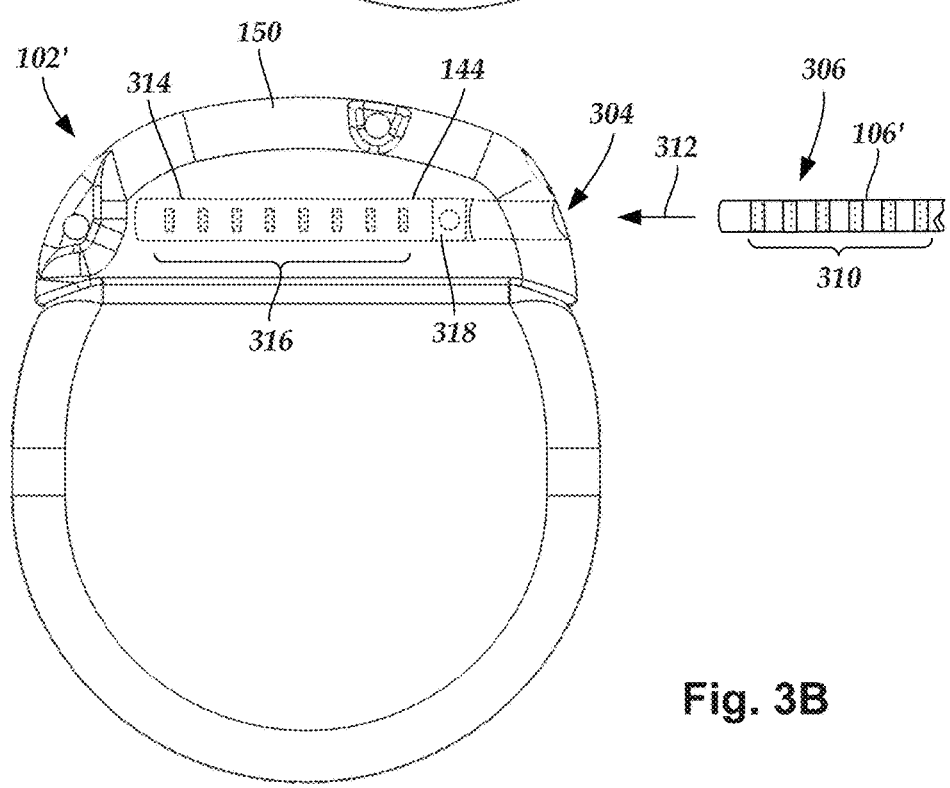
FIG. 3B is a schematic view of one embodiment of a connector disposed in the control module of FIG. 2, the connector configured and arranged to receive the proximal portion of one of the lead body of FIG. 2, according to the invention.

FIG. 3A is a schematic side view of one embodiment of a plurality of connectors 144 disposed on the control module 102. In at least some embodiments, the control module 102 includes two connectors 144. In at least some embodiments, the control module 102 includes four connectors 144. In FIG. 3A, proximal ends 306 of the plurality of lead bodies 106 are shown configured and arranged for insertion to the control module 102. FIG. 3B is a schematic side view of one embodiment of a single connector 144 disposed on the control module 102'. In FIG. 3B, the proximal end 306 of the single lead body 106' is shown configured and arranged for insertion to the control module 102'.

In FIGS. 3A and 3B, the one or more connectors 144 are disposed in the header 150. In at least some embodiments, the header 150 defines one or more lumens 304 into which the proximal end(s) 306 of the one or more lead bodies 106/106' with terminals 310 can be inserted, as shown by directional arrows 312, in order to gain access to the connector contacts disposed in the one or more connectors 144.

The one or more connectors 144 each include a connector housing 314 and a plurality of connector contacts 316 disposed therein. Typically, the connector housing 314 provides access to the plurality of connector contacts 316 via the lumen 304. In at least some embodiments, one or more of the connectors 144 further includes a retaining element 318 configured and arranged to fasten the corresponding lead body 106/106' to the connector 144 when the lead body 106/106' is inserted into the connector 144 to prevent undesired detachment of the lead body 106/106' from the connector 144. For example, the retaining element 318 may include an aperture 320 through which a fastener (e.g., a set screw, pin, or the like) may be inserted and secured against an inserted lead body 106/106'.

When the one or more lead bodies 106/106' are inserted into the one or more lumens 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connectors in control modules are found in, for example, U.S. Pat. Nos. 7,244,150 and 6,224,450, which are incorporated by reference.

Figure 3C:
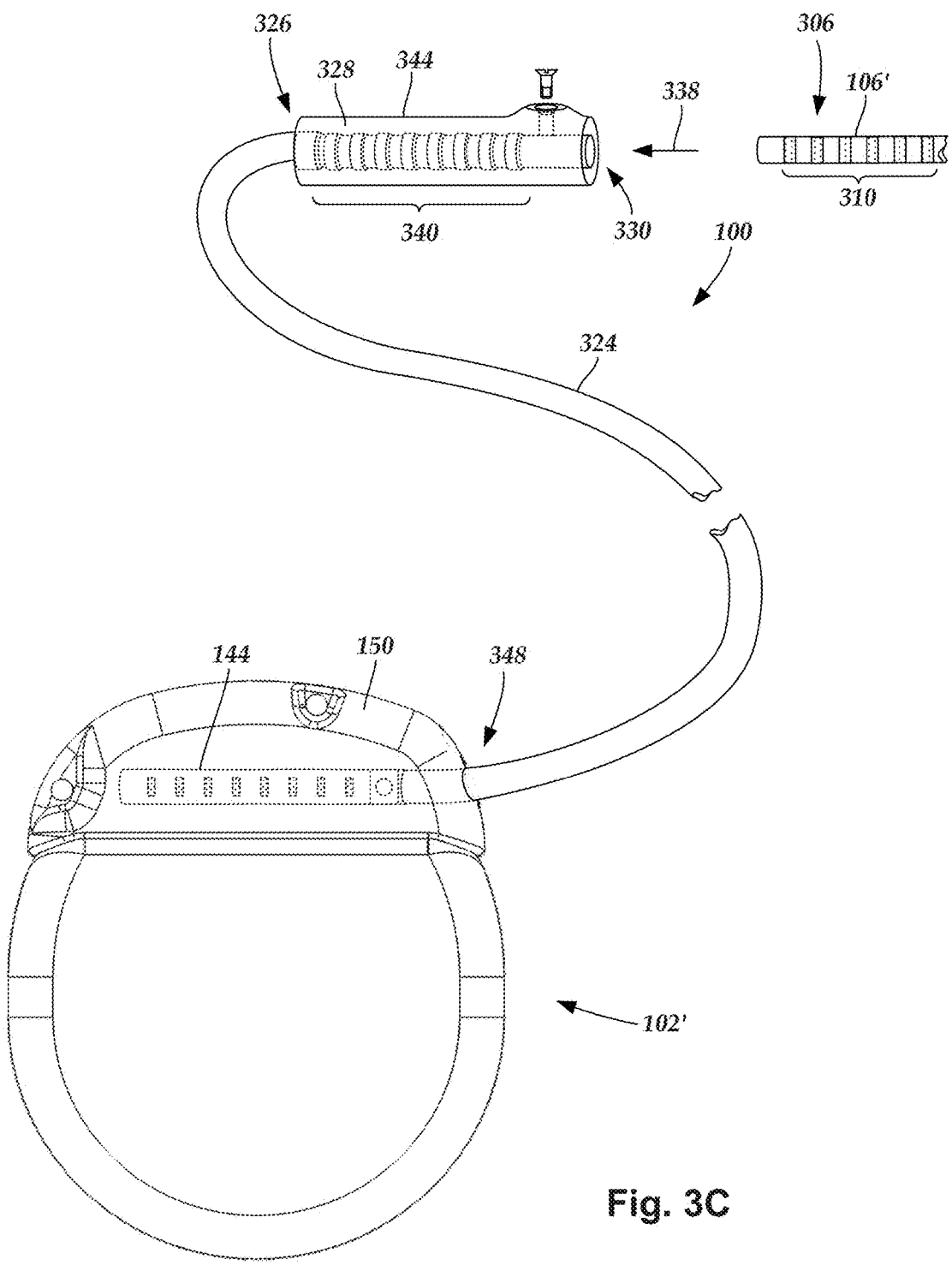
FIG. 3C is a schematic view of one embodiment of a proximal portion of the lead body of FIG. 2, a lead extension, and the control module of FIG. 2, the lead extension configured and arranged to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector 322 is disposed on a lead extension 324. The lead extension connector 322 is shown disposed at a distal end 326 of the lead extension 324. The lead extension connector 322 includes a connector housing 344. The connector housing 344 defines at least one lumen 330 into which a proximal end 306 of the lead body 106' with terminals 310 can be inserted, as shown by directional arrow 338. The lead extension connector 3" also includes a plurality of connector contacts 340. When the lead body 106' is inserted into the lumen 330, the connector contacts 340 disposed in the connector housing 344 can be aligned with the terminals 310 on the lead body 106 to electrically couple the lead extension 324 to the electrodes (134 of FIG. 1) disposed at a distal end (not shown) of the lead body 106'.

The proximal end of a lead extension can be similarly configured and arranged as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector disposed in another lead extension. In other embodiments (as shown in FIG. 3C), the proximal end 348 of the lead extension 324 is configured and arranged for insertion into the connector 144 disposed on the control module 102'.

It will be understood that the control modules 102/102' can receive either lead bodies 106/106' or lead extensions 324. It will also be understood that the electrical stimulation system 100 can include a plurality of lead extensions 324. For example, each of the lead bodies 106 shown in FIGS. 1 and 3A can, alternatively, be coupled to a different lead extension 324 which, in turn, are each coupled to different ports of a two-port control module, such as the control module 102 of FIGS. 1 and 3A.

Figure 4:
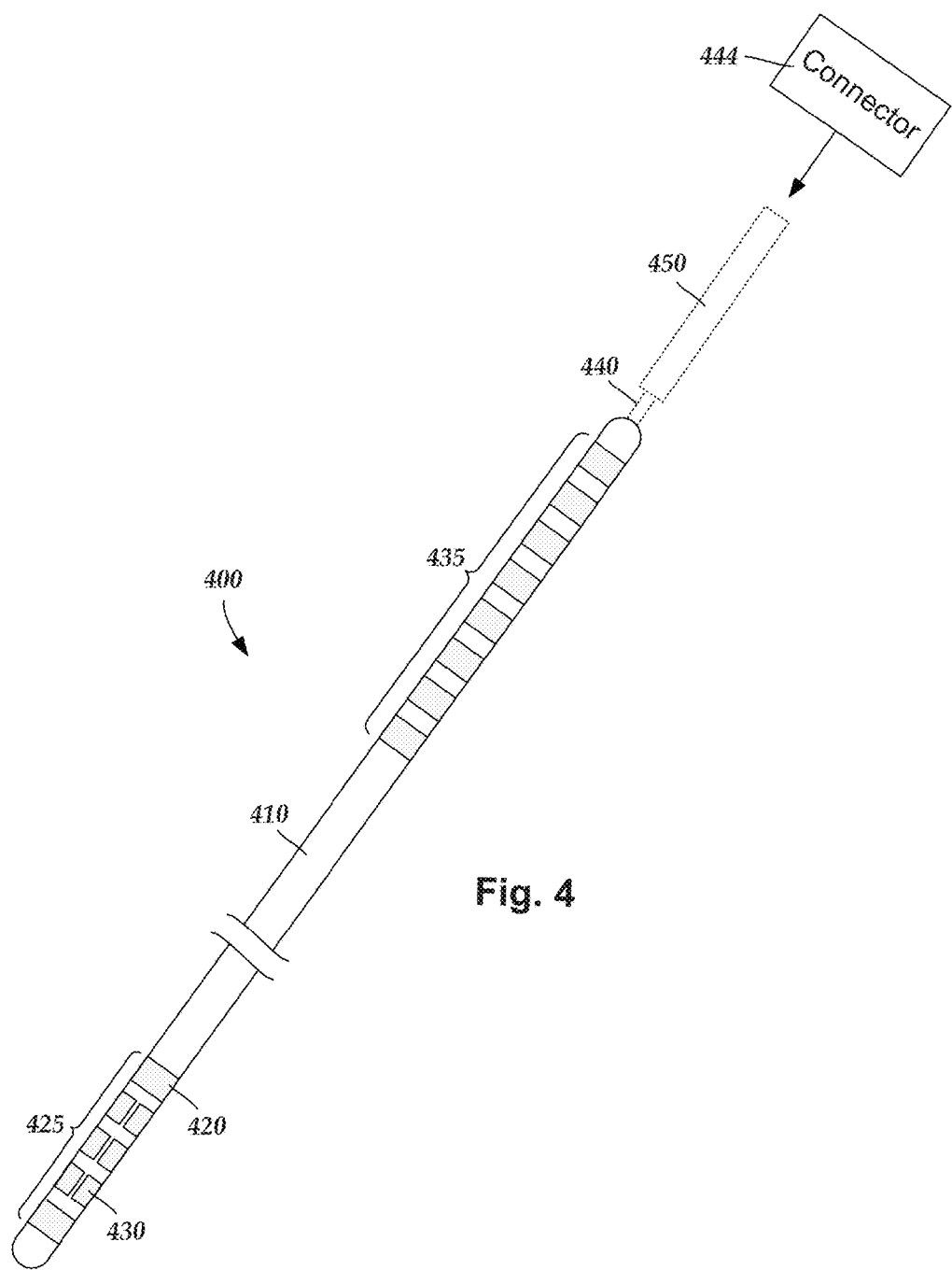
FIG. 4 is a schematic side view of yet another embodiment of an implantable medical device for brain stimulation, according to the invention.

Turning to FIG. 4, in the case of deep brain stimulation, the lead may include stimulation electrodes, recording electrodes, or a combination of both. At least some of the stimulation electrodes, recording electrodes, or both are provided in the form of segmented electrodes that extend only partially around the perimeter (for example, the circumference) of the lead. These segmented electrodes can be provided in sets of electrodes, with each set having electrodes circumferentially distributed about the lead at a particular longitudinal position.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead may include both recording electrodes and stimulation electrodes or electrodes may be used for both recording and stimulation.

FIG. 4 illustrates one embodiment of a device 400 for brain stimulation. The device includes a lead 410, a plurality of electrodes 425 disposed at least partially about a perimeter of the lead 410, a plurality of terminals 435, a connector 444 for connection of the electrodes to a control unit, and a stylet 440 for assisting in insertion and positioning of the lead in the patient's brain. The stylet 440 can be made of a rigid material. Examples of suitable materials for the stylet include, but are not limited to, tungsten, stainless steel, and plastic. The stylet 440 may have a handle 450 to assist insertion into the lead 410, as well as rotation of the stylet 440 and lead 410. The connector 444 fits over a proximal end of the lead 410, preferably after removal of the stylet 440.

In FIG. 4, the electrodes 425 are shown as including both ring electrodes, such as ring electrode 420, and segmented electrodes, such as segmented electrodes 430. In some embodiments, the electrodes 425 are all segmented. In other embodiments, the electrodes 425 are all ring-shaped. In FIG. 4, each of the terminals 435 is shown as being ring-shaped. The segmented electrodes of FIG. 4 are shown in sets of two, where the two segmented electrodes of a particular set are electrically isolated from one another and are circumferentially-offset along the lead 410. Any suitable number of segmented electrodes can be formed into a set including, for example, two, three, four, or more segmented electrodes.

Segmented electrodes can be used to direct stimulus current to one side, or even a portion of one side, of the lead. When segmented electrodes are used in conjunction with an implantable pulse generator that delivers current stimulus, current steering can be achieved to more precisely deliver the stimulus to a position around an axis of the lead (i.e., radial positioning around the axis of the lead). Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a segmented electrode array, current steering can be performed not only along a length of the lead but also around a perimeter of the lead.

This provides precise three-dimensional targeting and delivery of the current stimulus to neural target tissue, while potentially avoiding stimulation of other tissue. Examples of leads with segmented electrodes include U.S. Pat. Nos. 6,295,944; and 6,391,985; and U.S. Patent Applications Publication Nos. 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated herein by reference.

Figure 5E:
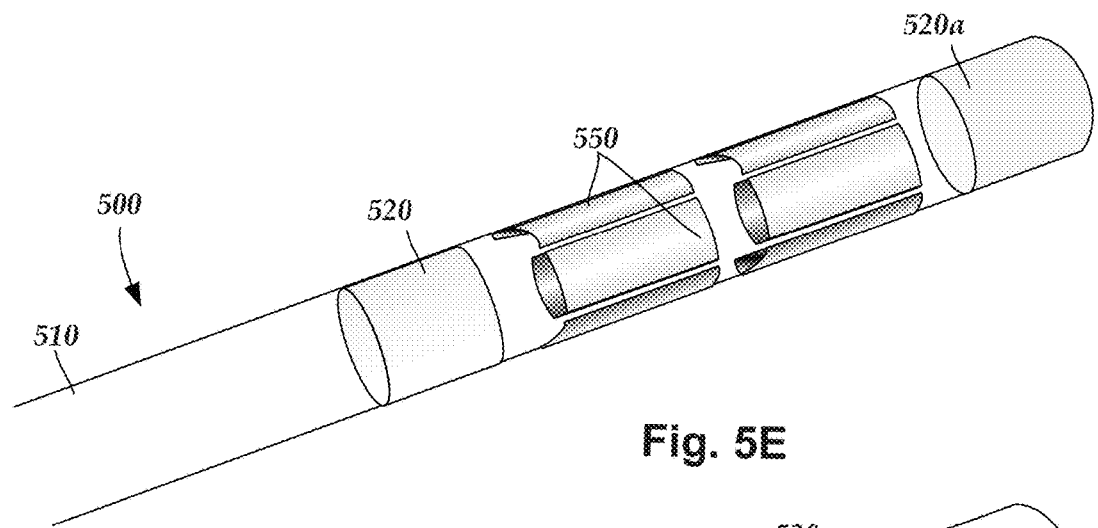
FIG. 5E is a schematic perspective view of a fifth embodiment of a distal end of a lead containing segmented electrodes, according to the invention.
Figure 5F:
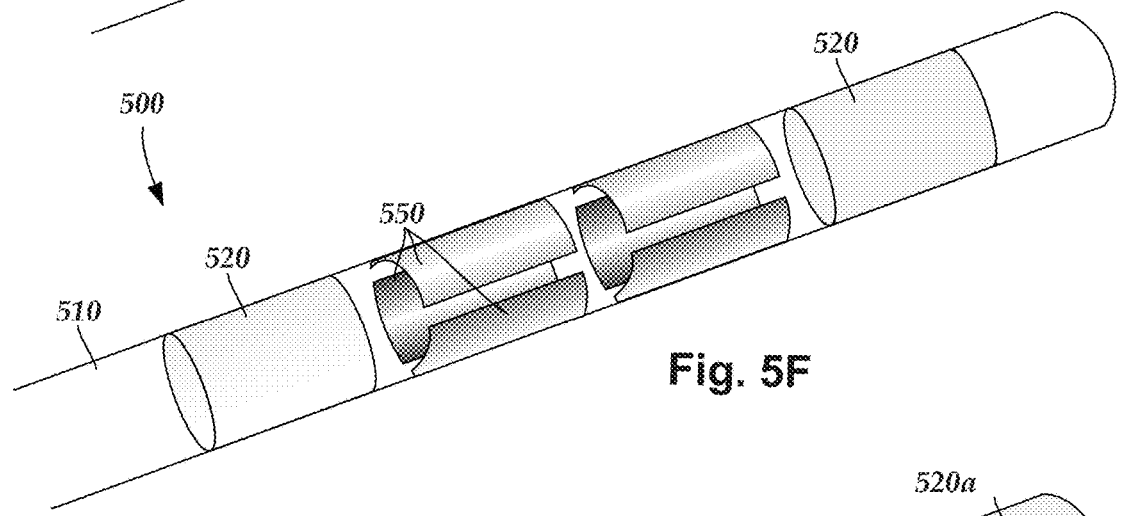
FIG. 5F is a schematic perspective view of a sixth embodiment of a distal end of a lead containing segmented electrodes, according to the invention.

FIGS. 5A-5H illustrate leads 500 with segmented electrodes 550, optional ring electrodes 520 or tip electrodes 520a, and a lead body 510. The sets of segmented electrodes 550 each include either two (FIG. 5B), three (FIGS. 5E-5H), or four (FIGS. 5A, 5C, and 5D) or any other number of segmented electrodes including, for example, three, five, six, or more. The sets of segmented electrodes 550 can be aligned with each other (FIGS. 5A-5G) or staggered (FIG. 5H).

When the lead 500 includes both ring electrodes 520 and segmented electrodes 550, the ring electrodes 520 and the segmented electrodes 550 may be arranged in any suitable configuration. For example, when the lead 500 includes two ring electrodes 520 and two sets of segmented electrodes 550, the ring electrodes 520 can flank the two sets of segmented electrodes 550 (see e.g., FIGS. 1, 5A, and 5E-5H). Alternately, the two sets of ring electrodes 520 can be disposed proximal to the two sets of segmented electrodes 550 (see e.g., FIG. 5C), or the two sets of ring electrodes 520 can be disposed distal to the two sets of segmented electrodes 550 (see e.g., FIG. 5D). One of the ring electrodes can be a tip electrode (see, tip electrode 520a of FIGS. 5E and 5G). It will be understood that other configurations are possible as well (e.g., alternating ring and segmented electrodes, or the like).

By varying the location of the segmented electrodes 550, different coverage of the target neurons may be selected. For example, the electrode arrangement of FIG. 5C may be useful if the physician anticipates that the neural target will be closer to a distal tip of the lead body 510, while the electrode arrangement of FIG. 5D may be useful if the physician anticipates that the neural target will be closer to a proximal end of the lead body 510.

Figure 5G:
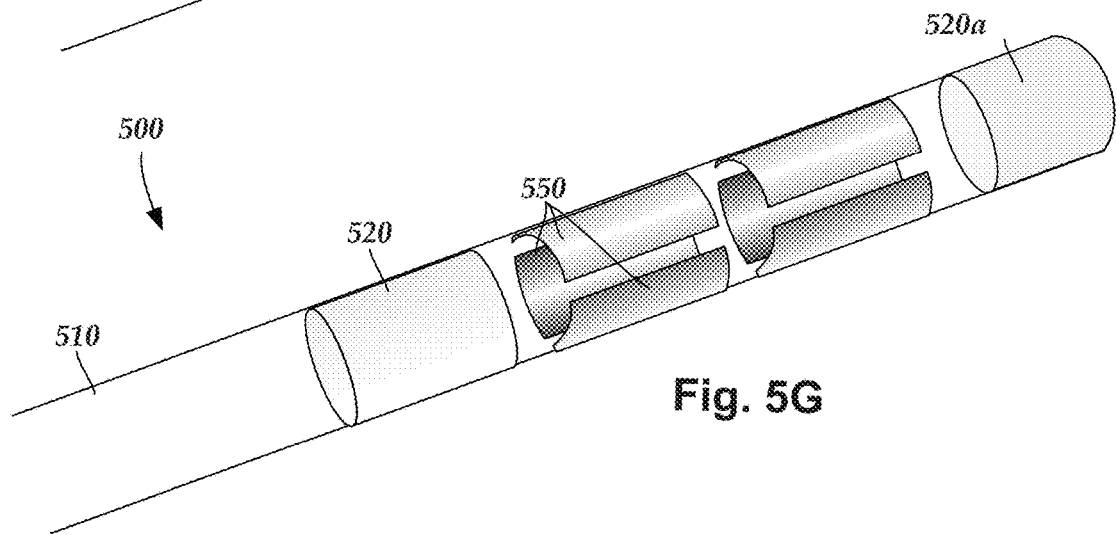
FIG. 5G is a schematic perspective view of a seventh embodiment of a distal end of a lead containing segmented electrodes, according to the invention.

Any combination of ring electrodes 520 and segmented electrodes 550 may be disposed on the lead 500. For example, the lead may include a first ring electrode 520, two sets of segmented electrodes; each set formed of four segmented electrodes 550, and a final ring electrode 520 at the end of the lead. This configuration may simply be referred to as a 1-4-4-1 configuration (FIGS. 5A and 5E ring electrodes 520 and segmented electrode 550). It may be useful to refer to the electrodes with this shorthand notation. Thus, the embodiment of FIG. 5C may be referred to as a 1-1-4-4 configuration, while the embodiment of FIG. 5D may be referred to as a 4-4-1-1 configuration. The embodiments of FIGS. 5F, 5G, and 5H can be referred to as a 1-3-3-1 configuration. Other electrode configurations include, for example, a 2-2-2-2 configuration, where four sets of segmented electrodes are disposed on the lead, and a 4-4 configuration, where two sets of segmented electrodes, each having four segmented electrodes 550 are disposed on the lead. The 1-3-3-1 electrode configuration of FIGS. 5F, 5G, and 5H has two sets of segmented electrodes, each set containing three electrodes disposed around the perimeter of the lead, flanked by two ring electrodes (FIGS. 5F and 5H) or a ring electrode and a tip electrode (FIG. 5G). In some embodiments, the lead includes 16 electrodes. Possible configurations for a 16-electrode lead include, but are not limited to 4-4-4-4; 6-8; 5-3-3-3-3-1 (and all rearrangements of this configuration); and 2-2-2-2-2-2-2-2. Any other suitable segmented electrode arrangements (with or without ring electrodes) can be used including, but not limited to, those disclosed in U.S. Provisional Patent Application Ser. No. 62/113,291 and U.S. Patent Applications Publication Nos. 2012/0197375 and 2015/0045864, all of which are incorporated herein by reference.

In at least some embodiments, a lead with 16 electrodes also includes 16 terminals. Many conventional control modules and connectors are designed to accept a proximal end of a lead or lead extension with an array of eight terminals. To instead have 16 terminals could extend the length of the proximal end of the lead or lead extension and a consequent increase in the size of connector or control module.

Instead, in at least some embodiments it may be advantageous to design an elongate member (e.g., a lead, lead extension, splitter, adaptor, or the like) with segmented terminals. In at least some embodiments, the elongate member also includes segmented electrodes. Utilizing segmented terminals may reduce the physical size of the terminal array when compared to conventional terminal arrays with ring-shaped terminals. Consequently, the portion of the elongate member that is inserted into a connector to make electrical contact with the pulse generator can be reduced, as compared to conventional electrical stimulation systems. Alternately, the number of terminals that can be disposed along a proximal portion of an elongate member and that can be inserted into a conventionally-sized connector may be increased from conventional electrical stimulation systems. Some examples of such arrangements are found in, for example, U.S. Provisional Patent Application Ser. No. 62/113,291, incorporated herein by reference.

Although the embodiments described below are presented as leads, it will be understood that the arrangement of segmented terminals, a retention sleeve, and an alignment slit, described below, can also be applied to a lead extension or other elongate member having terminals. In general, any elongate member can have first contacts (for example, electrode for a lead or conductive contacts for a lead extension) disposed along a distal portion of the elongate member and second segmented contacts (for example, segmented terminals) disposed along a proximal portion of the elongate member.

Figures 6A, 6B, 6C, 6D, 6E:
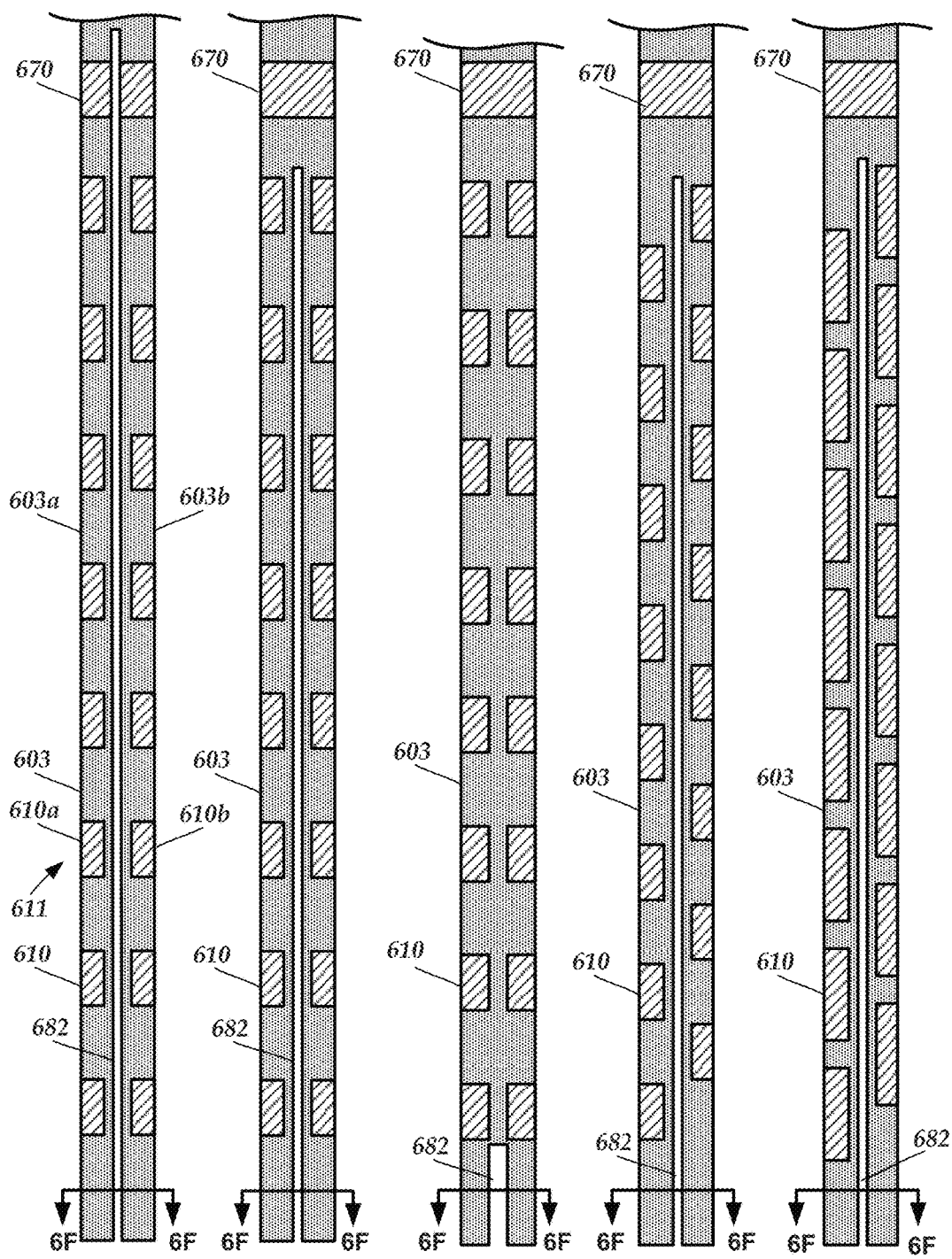
FIG. 6A is a schematic side view of one embodiment of a proximal end of a lead containing segmented terminals and an alignment slit, according to the invention.
FIG. 6B is a schematic side view of a second embodiment of a proximal end of a lead containing segmented terminals and an alignment slit, according to the invention.
FIG. 6C is a schematic side view of a third embodiment of a proximal end of a lead containing segmented terminals and an alignment slit, according to the invention.
FIG. 6D is a schematic side view of a fourth embodiment of a proximal end of a lead containing segmented terminals and an alignment slit, according to the invention.
FIG. 6E is a schematic side view of a fifth embodiment of a proximal end of a lead containing segmented terminals and an alignment slit, according to the invention.
Figure 6F:
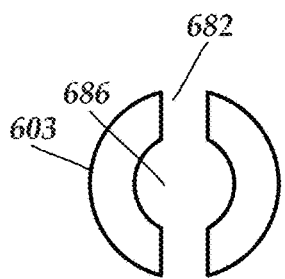
FIG. 6F is a schematic cross-sectional view of any one of the leads of FIGS. 6A-6E, according to the invention.

FIG. 6A illustrates one embodiment of a proximal portion of a lead 603 (or other elongate member) with an array of segmented terminals 610 and an optional retention sleeve 670. To ensure proper alignment between of the lead 603 (or other elongate member) in a connector 644 (FIGS. 7A-7D) so that each terminal is electrically connected to a single connector contact, the lead includes an alignment slit 682 formed along a portion of the proximal end of the lead. The alignment slit 682 extends completely through the lead 603 and intersects a central lumen 686 (or stylet lumen) of the lead, as shown in FIG. 6F. The alignment slit 682 separates the proximal portion of the lead into at least two sections 603a, 603b that are laterally spaced-apart and separated by the alignment slit.

The segmented terminals 610 can be formed in sets of two or more terminals at a same position along the longitudinal axis of the lead. Each of the segmented terminals of a particular set extends around less than (for example, no more than 45%, 40%, 33%, 30%, or 25% of) the entire perimeter of the elongate member. The segmented terminals of the set are not in electrical contact with one another and are circumferentially-offset from one another along the elongate member. In at least some embodiments, the terminal array includes at least one segmented terminal set, such as segmented terminal set 611 which, in turn, includes multiple segmented terminals 610, such as segmented terminals 610a and 610b. In some embodiments, a set of segmented terminals can have two, three, four, or more segmented terminals disposed at the same position along the longitudinal axis of the elongate member, but circumferentially offset from each other. In at least some embodiments, the alignment slit 682 extends between at least two of the segmented terminals of one or more (or even each) of the sets of segmented terminals. In at least some of these embodiments, each set includes exactly two segmented terminals.

In some embodiments, the terminal array is formed exclusively from segmented terminals. In other embodiments, the terminal array includes a combination of one or more ring-shaped terminals and one or more segmented terminal sets.

The terminal array can include any suitable number of segmented terminal sets 611 including, for example, one, two, three, four, five, six, seven, eight, nine, ten eleven, twelve, thirteen, fourteen, fifteen, sixteen, or more segmented-terminal sets. In FIG. 6A, eight segmented terminal sets 611 are shown disposed along the lead 603.

In at least some embodiments, the elongate member includes a single proximal portion and multiple distal portions. One advantage of implementing segmented terminals is that it may increase the number of terminals disposed along a lead from conventional leads. The increased number of terminals may enable the lead to be designed with multiple distal portions. Where a different electrode array is disposed along each of the distal portions, and where electrodes of each of the multiple electrode arrays are coupled to terminals disposed along a single proximal portion. Such a design may be useful, for example, in deep brain stimulation where bilateral stimulation may be desirable.

When the lead has multiple distal portions and a single proximal portion with segmented terminals, the single proximal portion can be received by a single connector port. Such an arrangement enables each of multiple electrode arrays disposed along different distal portions to be operated by a single control module. Additionally, much a design enables multiple electrode arrays to be controlled by a single control module via a single connector with a single lead-receiving port.

In FIG. 6A, the alignment slit 682 extends from the proximal end of the lead to a point beyond the retention sleeve 670. The alignment slit 682 separates the terminals 610a, 610b in each set 611 and divides the retention sleeve 670 into two parts that are laterally spaced-apart and separated from each other by the alignment slit. FIGS. 6B, 6C, 6D, and 6E illustrate alternative embodiments of the lead 603 and the alignment slit 682. In the embodiments of FIGS. 6B, 6D, and 6E, the alignment slit 682 terminates distal to all of the terminals 610, but proximal to the retention sleeve 670. In the embodiment of FIG. 6C, the alignment slit 682 terminates proximal to all of the terminals 610. It will be understood that in other embodiments, the alignment slit can terminate anywhere along the array of terminals 610.

In FIGS. 6A-6C, the terminal 610 of each set are aligned with each other to form longitudinal columns (i.e., columns parallel to the longitudinal axis of the lead) of terminals that are aligned. FIGS. 6D and 6E illustrate arrangements of segmented terminals 610 in longitudinal columns that are longitudinally offset from each other (for example, the terminals on the left of FIGS. 6D and 6E are longitudinally offset from those on the right). In FIG. 6D the terminals of different longitudinal columns do not overlap and in FIG. 6E the terminals of different longitudinal columns do overlap. It will be recognized that other arrangements of segmented terminals, including any of those arrangements described above with respect to arrangements of segmented terminals, can be used.

Figure 7A:
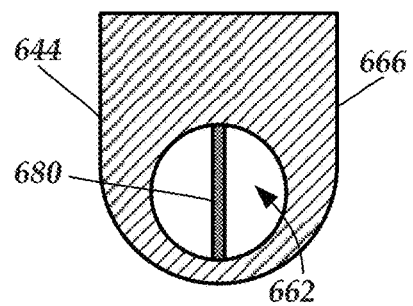
FIG. 7A is schematic end view of one embodiment of a connector for receiving a lead containing segmented terminals, according to the invention.
Figure 7B:
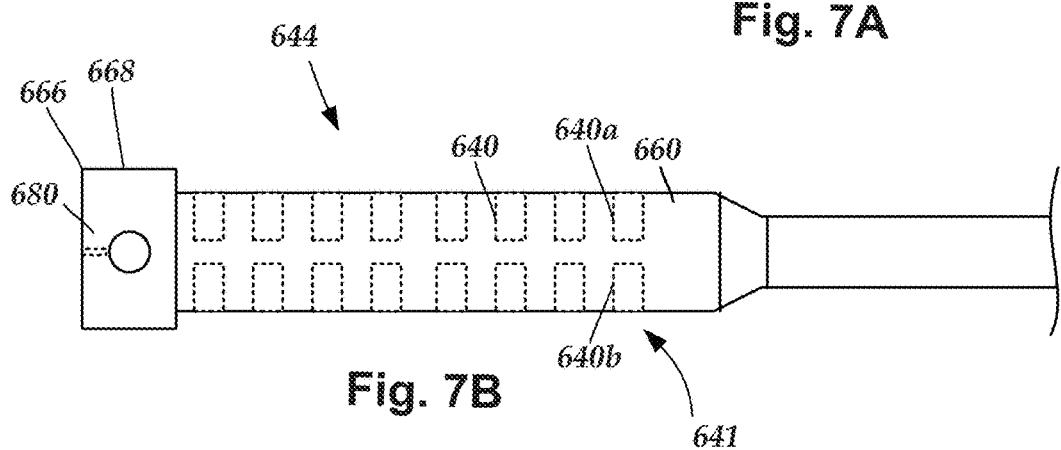
FIG. 7B is schematic side view of one embodiment of a connector for receiving a lead containing segmented terminals, according to the invention.
Figure 7C:
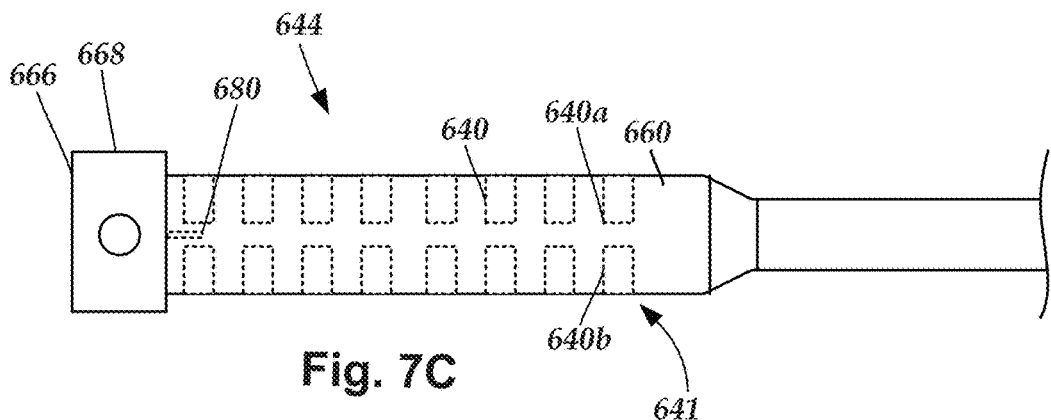
FIG. 7C is schematic side view of a second embodiment of a connector for receiving a lead containing segmented terminals, according to the invention.
Figure 7D:
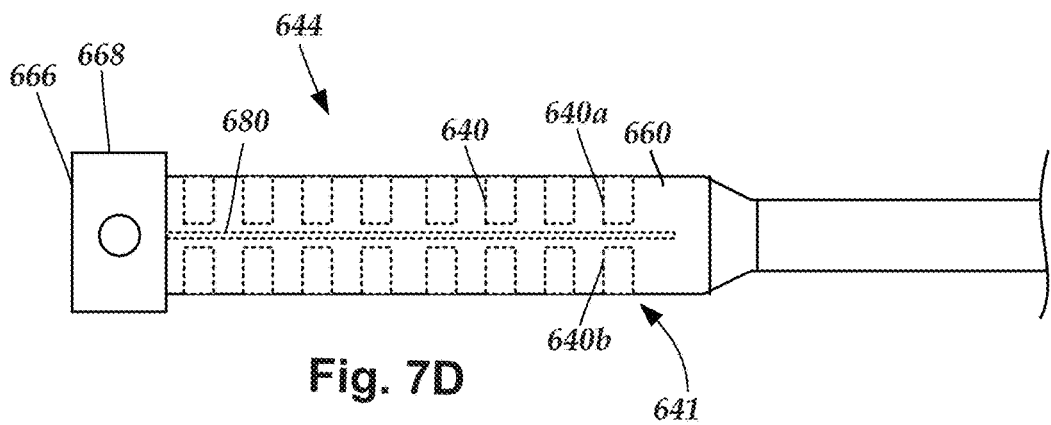
FIG. 7D is schematic side view of a third embodiment of a connector for receiving a lead containing segmented terminals, according to the invention.

Turning to FIGS. 7A and 7B, the proximal portion of the elongate member, such as the lead 603 (FIGS. 6A-6F), is typically inserted into a connector 644 disposed on or along a lead extension, control module, adaptor, splitter, or the like. The connector 644 includes segmented connector contacts 640 suitable for coupling with the segmented terminals. The connector 644 includes an elongated connector housing 660 that defines a connector lumen 662 suitable for receiving a portion of an elongate member, such as the lead 603

(FIG. 6A-6F); a lead extension (e.g., 324 in FIG. 3C); or the like. The connector 644 also include an alignment structure 680 (FIG. 6C—for example, a pin, blade, seal, wall, rod, or rail) that extends into the connector lumen 662 (and, in at least some embodiments, across the entire diameter of the connector lumen) and can be used to align the lead with the connector by mating with the alignment slit 682 of the lead. Although the illustrated connector lumen has a circular cross-section, it will be understood that lumens with other cross-sections (and leads with non-circular cross-sections) can also be used including, but not limited to, oval, square, rectangular, triangular, pentagonal, hexagonal, octagonal, cruciform, or any other suitable regular or irregular cross-sectional shape.

Multiple connector contacts 640 are disposed in a spaced-apart relationship along the longitudinal length of the connector housing 660 such that the connector contacts are exposed to the connector lumen 662 (FIG. 7A) and individually attached to an array of conductive members (for example, wires, pins, traces, terminals, or the like) that couple the connector contacts to other components. When, for example, the connector 644 is disposed on a lead extension (e.g., 324 in FIG. 3C), the conductive members (for example, wires or other conductors) may couple the connector contacts to lead extension terminals. When, for example, the connector 644 is disposed on a control module, the conductive members (for example, wires, traces, pins, or the like) may couple the connector contacts 640 to the electronic subassembly (110 in FIG. 1). In at least some embodiments, the conductive members 664 couple the connector contacts 640 to the electronic subassembly (110 in FIG. 1), via feedthrough pins extending through the sealed housing (114 in FIG. 1).

In at least some embodiments, the segmented connector contacts 640 can be formed in sets of two or more terminals at a same position along the longitudinal axis of the connector lumen 662. Each of the segmented connector contacts of a particular set extends around less than (for example, no more than 45%, 40%, 33%, 30%, or 25% of) the entire perimeter of the connector lumen. The segmented connector contacts of the set are not in electrical contact with one another and are circumferentially offset from one another along the connector lumen. In at least some embodiments, the connector contact array includes at least one segmented connector contacts set, such as segmented connector contacts set 641 which, in turn, includes multiple segmented connector contacts 640, such as segmented terminals 640a and 640b. In some embodiments, a set of segmented connector contacts can have two, three, four, or more segmented connector contacts disposed at the same position along the longitudinal axis of the connector lumen, but circumferentially offset from each other.

Optionally, a retention block 666 is disposed along the connector 644. The retention block 666 can be used to facilitate retention of an elongate member when the elongate member is inserted into the connector lumen 662. In at least some embodiments, the retention block 666 defines a fastening aperture 668 configured to receive a fastener (e.g., a set screw, pin, or the like) which can engage the optional retention sleeve 670 (FIG. 6A) of the lead. In at least some embodiments, the fastener, when received by the fastener aperture 668, is configured to tighten against a portion of the elongate member (e.g., a retention sleeve) when the elongate member is inserted into the connector lumen 662.

The connector 644 includes an alignment structure 680 that mates with or fits within the alignment slit 682 of the lead 603. Engagement of the alignment structure 680 of the connector 644 with the alignment slit 682 of the lead 603 ensures that the lead and connector have the proper rotational alignment for correctly coupling the segmented terminals 610 of the lead 603 with the connector contacts 640 of the connector 644.

In the embodiment of FIG. 7B, the alignment structure 680 is disposed in the retention block 666. This particular arrangement is useful with the lead 603 of FIG. 6A where the alignment slit 670 extends through the retention sleeve 670. The alignment structure 680 can be placed elsewhere in the connector 644. For example, in the embodiment illustrated in FIG. 7C, the alignment structure 680 is placed outside the retention block 666. This arrangement can be used with any of the leads illustrated in FIGS. 6A, 6B, 6D, and 6E. In the embodiment illustrated in FIG. 7D, the alignment structure 680 extends between all of the connector contacts 640 and can be used with any of the leads illustrated in FIGS. 6A, 6B, 6D, and 6E. In other embodiments, the alignment structure 680 may extend between fewer than all of the connector contacts 640. The alignment structure 680 can be placed in other portions of the connector lumen 662, such as near the end of the connector lumen, which would be required for use with the lead illustrated in FIG. 6C.

Any suitable type of connector contact 640 can be used in connector 644. Examples of suitable connector contacts and connectors can be found in, for example, U.S. Provisional Patent Application Ser. Nos. 62/077,762; 62/077,784; and 62/113,291, all of which are incorporated herein by reference.

FIGS. 8A-8D illustrate, in cross-section, embodiments of connector contacts 840 (two connector contacts are illustrated in each Figure) for use in a connector (such as connector 644 of FIGS. 7A-7D) having a connector wall 861 that defines the connector lumen 862 and an alignment structure 880. If FIGS. 8A and 8B, the connector contacts 840 are arced metal contacts. These connector contacts form an arc ranging from, for example, 90 to 175 degrees or 100 to 160 degrees.

Figure 8A:
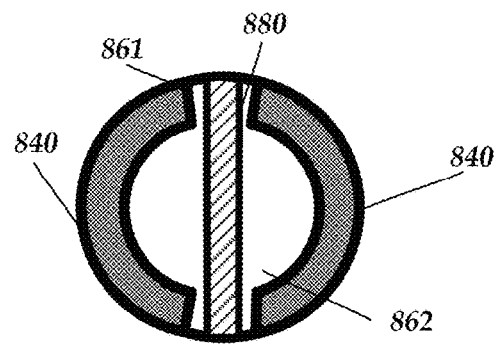
FIG. 8A is a schematic cross-sectional view of one embodiment of segmented connector contacts and a connector lumen, according to the invention.
Figure 8B:
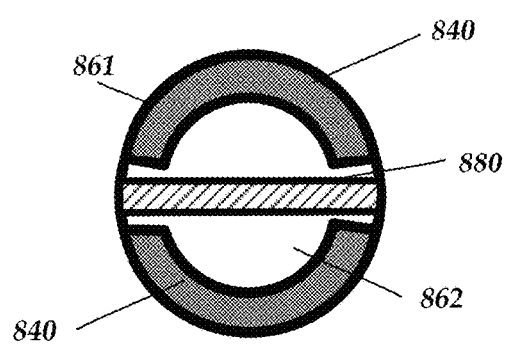
FIG. 8B is a schematic cross-sectional view of a second embodiment of segmented connector contacts and a connector lumen, according to the invention.
Figure 8C:
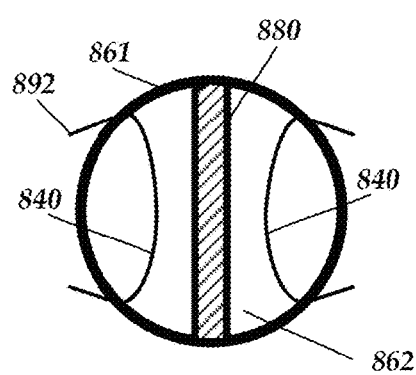
FIG. 8C is a schematic cross-sectional view of a third embodiment of segmented connector contacts and a connector lumen, according to the invention.
Figure 8D:
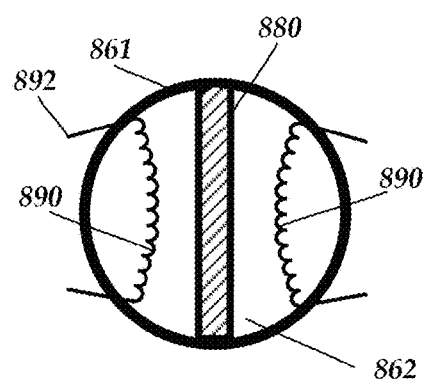
FIG. 8D is a schematic cross-sectional view of a fourth embodiment of segmented connector contacts and a connector lumen, according to the invention.

In FIG. 8C, the connector contacts 840 are leaf springs 890 disposed within the connector lumen 862 with one or more legs 892 that extend through the connector wall 861 to make electrical connection (for example, by welding, soldering, or the like) with other portions (for example, conductive members 664 of FIG. 6C) of the connector. In FIG. 8D, the connector contacts 840 are coiled leaf springs 891 disposed within the connector lumen 862 with one or more legs 892 that extend through the connector wall 861 to make electrical connection with other portions of the connector.

Figure 9A:
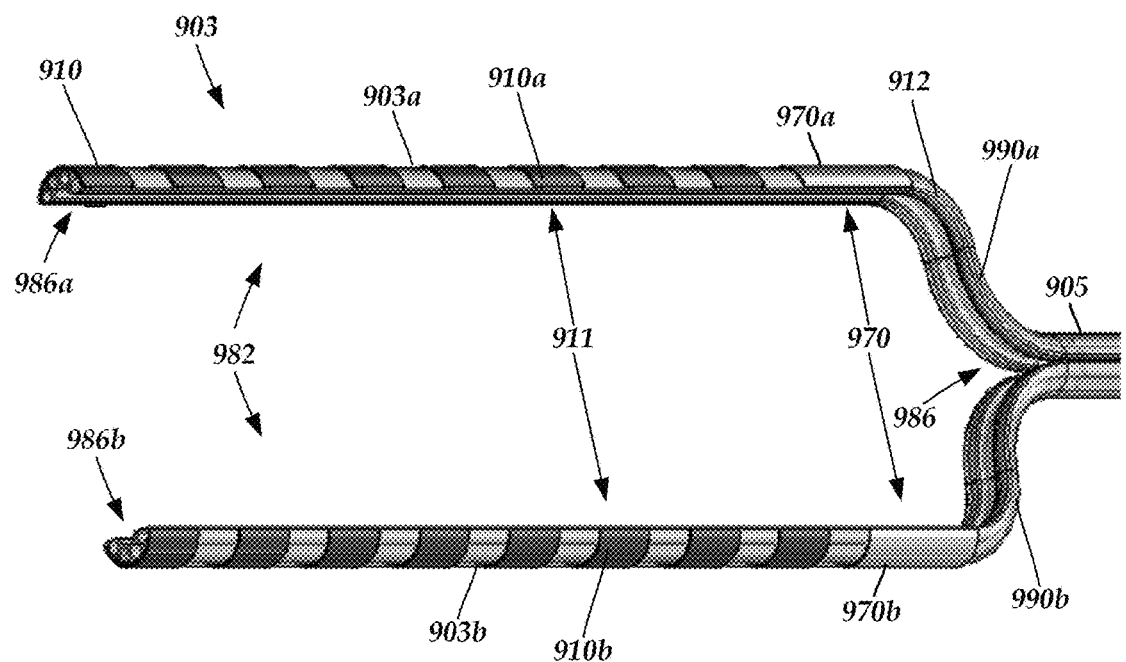
FIG. 9A is a schematic perspective side view of a sixth embodiment of a proximal end of a lead containing segmented terminals and an alignment slit, according to the invention.

FIG. 9A illustrates the proximal end portion of another embodiment of lead 903 with an array of segmented terminals 910, an optional retention sleeve 970, and an alignment slit 982. The proximal end portion of the lead 903 is divided into two branches 903a, 903b by the alignment slit 982 with terminals 910a, 910b disposed on each branch and, optionally, a portion 970a, 970b of the retention sleeve. Each branch 903a, 903b includes a bendable section 990a, 990b distal to all of the terminals 910 and the optional retention sleeve 970. The bendable sections 990a, 990b can allow the two branches 903a, 930b to be inserted into two different connectors. The two branches 903a, 903b join together to form a joined portion 905 of the lead 903. The lead 903 can also include a central lumen 986 with separate channels 986a, 986b form in the respective branches 903a, 903b. In at least some embodiments, the two branches 903a, 903b have a hemispherical lateral cross-sectional shape which could be considered an arc-shaped lateral cross-sectional shape if the central lumen 986 is ignored.

Figure 9B:
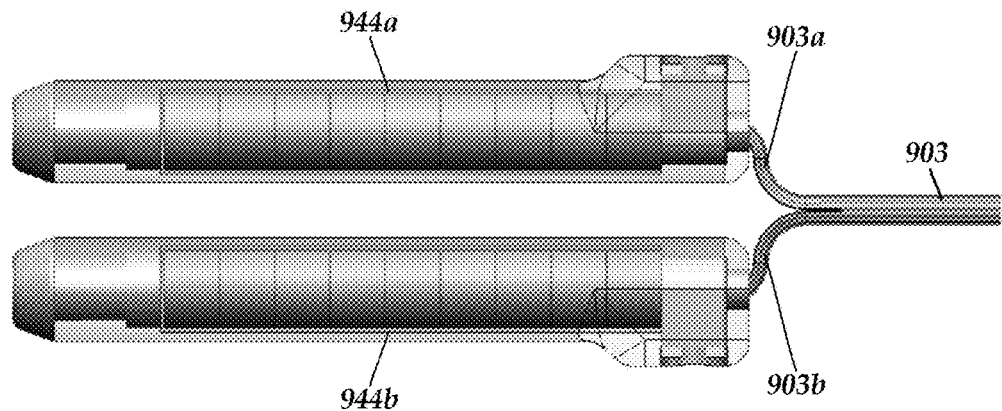
FIG. 9B is a schematic side view of the proximal end of the lead of FIG. 9A inserted into two connectors, according to the invention.

Each branch 903a, 903b can fit into a different connector 944a, 944b, as illustrated in FIG. 9B. The two different connectors 944a, 944b can be two connectors formed as part of control module (for example, control module 902) or two connectors of a single lead extension or connectors on two different lead extensions (see, for example, lead extension 324 of FIG. 3C). In at least some embodiments, the connector lumens of the two connectors 944a, 944b that receive the branches 903a, 903b can have a hemispherical or arc-shaped lateral cross-sectional shape.

The segmented terminals 910 can be formed in sets of two or more terminals at a same position along the longitudinal axis of the lead. The segmented terminals of the set are not in electrical contact with one another and are circumferentially-offset from one another along the elongate member. In at least some embodiments, the terminal array includes at least one segmented terminal set, such as segmented terminal set 911 which, in turn, includes multiple segmented terminals 910, such as segmented terminals 910a and 910b. In some embodiments, a set of segmented terminals can have two, three, four, or more segmented terminals disposed at the same position along the longitudinal axis of the elongate member, but circumferentially offset from each other.

The terminal array can include any suitable number of segmented terminal sets 911 including, for example, one, two, three, four, five, six, seven, eight, nine, ten eleven, twelve, thirteen, fourteen, fifteen, sixteen, or more segmented-terminal sets. In FIG. 9A, eight segmented terminal sets 911 are shown disposed along the lead 903.

In at least some embodiments, the bendable sections 990a, 990b are permanently bent in the desired configuration. In other embodiments, the bendable sections 990a, 990b are sufficiently flexible to allow a practitioner to modify the bends in the bendable sections, but still maintain the modified bends when the branch is released by the practitioner. In yet other embodiments, the bendable sections 990a, 990b are sufficiently flexible to be bend by the practitioner, but do not maintain the bends when the branch is released by the practitioner.

Figure 10A:
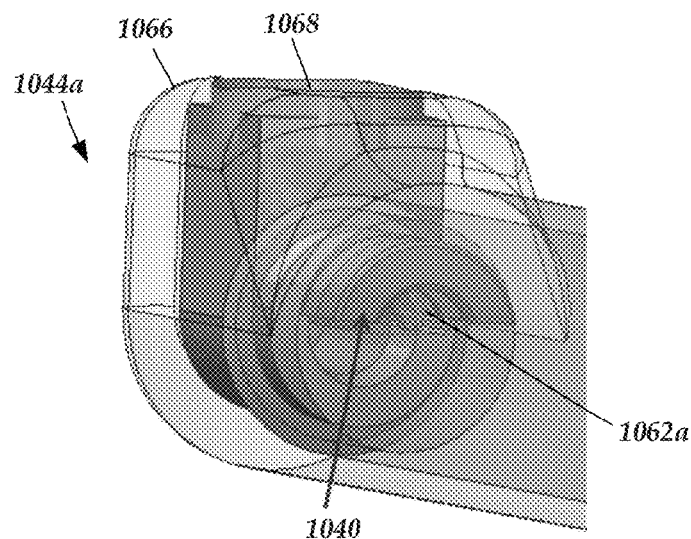
FIG. 10A is a schematic perspective view of a distal portion of a connector for receiving a portion of the proximal end of the lead of FIG. 9A with the body rendered translucent to illustrated inner components of the connector, according to the invention.
Figure 10B:
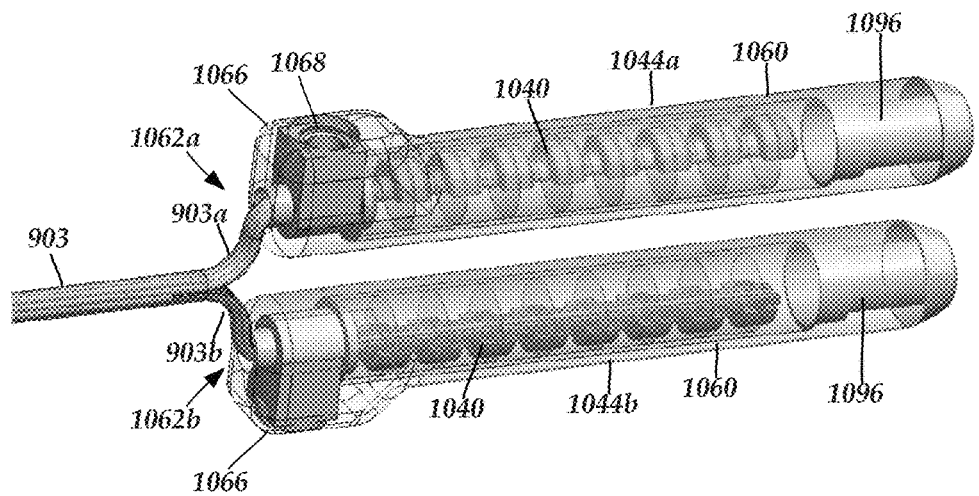
FIG. 10B is a schematic side view of the proximal end of the lead of FIG. 9A inserted into two connectors with the bodies of the connectors rendered translucent to illustrated inner components of the connectors, according to the invention.

FIGS. 10A and 109 illustrate one embodiment of connectors 1044a, 1044b Where the body 1060 of the connectors is translucent to facilitate a view of the interior components of the connectors. Each connector 1044a, 1044b has a connector lumen 1062a, 1062b that, in at least some embodiments, has a shape similar to the branch 903a, 903b of the lead 903 (for example, a hemispherical shape.) Each connector 1044, 1044a includes connector contacts 1040 suitable for coupling with the segmented terminals. Optionally, a retention block 1066 is disposed along each connector 1044a, 1044b. The retention block 1066 can be used to facilitate retention of an elongate member when the elongate member is inserted into the connector lumen 1062a, 1062b. In at least some embodiments, the retention block 1066 defines a fastening aperture 1068 configured to receive a fastener (e.g., a net screw, pin, or the like) which can engage the optional retention sleeve 1070 of the lead. In at least some embodiments, the fastener, when received by the fastener aperture 1068, is configured to tighten against a portion of the elongate member (e.g., a retention sleeve) when the elongate member is inserted into the connector lumen 1062a, 1062b. Each connector can also optionally include a stop 1096 which provides aback stop for insertion of the lead or lead extension into the connector In the illustrated embodiment, the connector contacts 1040 are formed as circular arcs of 180 degrees or less, but it will be understood that a full cylinder (or circular arc of greater than 180 degrees can be used for the connector contact. In addition, any of the connector contacts illustrated in FIGS. 8A-8D can be used but with only a single connector contact at each position along the connector, instead of two connector contacts as illustrated in FIGS. 8A-8D.

With respect to leads with the terminal arrays illustrated in FIGS. 6A-6E and 9A, the corresponding electrodes can be segmented electrodes, ring electrodes, other electrodes disclosed herein, or any other suitable electrode, or any combination thereof. In particular, although the terminals of a lead may be or part segmented terminals, the corresponding electrodes may be segmented electrodes, non-segmented electrodes, or any combination thereof.

Figure 11:
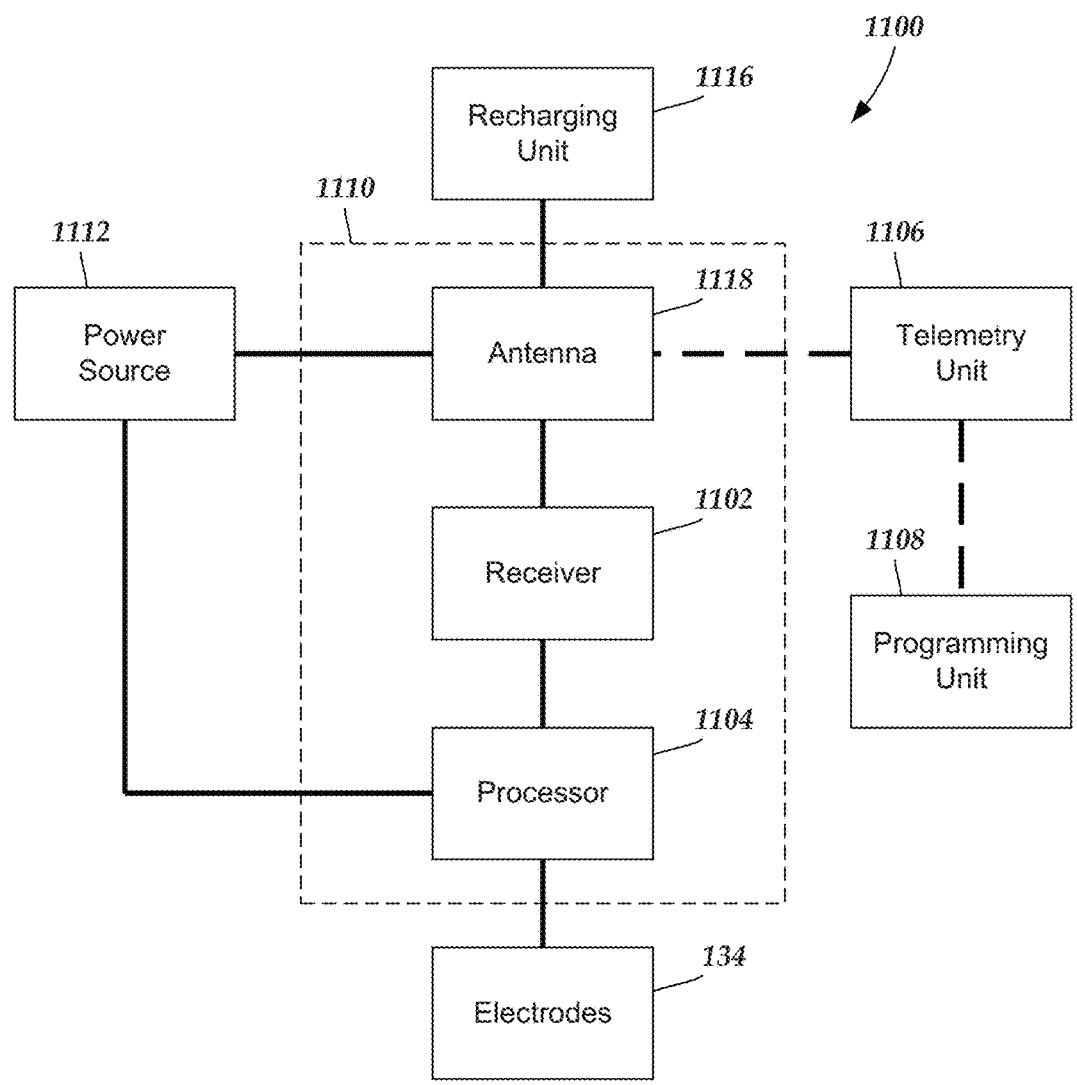
FIG. 11 is a schematic overview of one embodiment of components of an electrical stimulation system, according to the invention.

FIG. 11 is a schematic overview of one embodiment of components of an electrical stimulation system 1100 including an electronic subassembly 1110 disposed within a control module. It will be understood that the electrical stimulation system can include more, fewer, or different components and can have a variety of different configurations including those configurations disclosed in the stimulator references cited herein.

Some of the components (for example, power source 1112, antenna 118, receiver 1102, and processor 1104) of the electrical stimulation system can be positioned on one or more circuit boards or similar carriers within a sealed housing of an implantable pulse generator, if desired. Any power source 1112 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1118 or a secondary antenna. The external power source can be in a device that is mounted on the skin of the user or in a unit that is provided near the user on a permanent or periodic basis.

If the power source 1112 is a rechargeable battery, the battery may be recharged using the optional antenna 1118, if desired. Power can be provided to the battery for recharging by inductively coupling the battery through the antenna to a recharging unit 1116 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1104 is generally included Co control the timing and electrical characteristics of the electrical stimulation system. For example, the processor 1104 can, if desired, control one or more of the timing, frequency, strength, duration, and waveform of the pulses. In addition, the processor 1104 can select which electrodes can be used to provide stimulation, if desired. In some embodiments, the processor 1104 may select which electrode(s) are cathodes and which electrode(s) are anodes. In some embodiments, the processor 1104 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1108 that, for example, allows modification of pulse characteristics. In the illustrated embodiment, the processor 1104 is coupled to a receiver 1102 which, in turn, is coupled to the optional antenna 1118. This allows the processor 1104 to receive instructions from an external source to, for example, direct the pulse characteristics and the selection of electrodes, if desired.

In one embodiment, the antenna 1118 is capable of receiving signals (e.g., RF signals) from an external telemetry unit 1106 which is programmed by a programming unit 1108. The programming unit 1108 can be external to, or part of, the telemetry unit 1106. The telemetry unit 1106 can be a device that is worn on the skin of the user or can be carried by the user and can have a form similar to a pager, cellular phone, or remote control, if desired. As another alternative, the telemetry unit 1106 may not be worn or carried by the user but may only be available at a home station or at a clinician's office. The programming unit 1108 can be any unit that can provide information to the telemetry unit 1106 for transmission to the electrical stimulation system 1100. The programming unit 1108 can be part of the telemetry unit 1106 or can provide signals or information to the telemetry unit 1106 via a wireless or wired connection. One example of a suitable programming unit is a computer operated by the user or clinician to send signals to the telemetry unit 1106.

The signals sent to the processor 1104 via the antenna 1118 and receiver 1102 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1100 to cease operation, to start operation, to start charging the battery, or to stop charging the battery. In other embodiments, the stimulation system does not include an antenna 1118 or receiver 1102 and the processor 1104 operates as programmed.

Optionally, the electrical stimulation system 1100 may include a transmitter (not shown) coupled to the processor 1104 and the antenna 1118 for transmitting signals back to the telemetry unit 1106 or another unit capable of receiving the signals. For example, the electrical stimulation system 1100 may transmit signals indicating whether the electrical stimulation system 1100 is operating properly or not or indicating when the battery needs to be charged or the level of charge remaining in the battery. The processor 1104 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead or lead extension, comprising:
    a body having an outer surface, a proximal end, a proximal portion, at least one distal portion, a perimeter, and a longitudinal length, the body defining an alignment slit extending distally from the proximal end of the body and splitting the proximal portion of the body into two transversely spaced-apart, non-cylindrical arc sections;
    a plurality of first contacts disposed along the at least one distal portion of the body;
    a plurality of non-cylindrical segmented second contacts disposed along the proximal portion of the body, wherein each segmented second contact extends around less than the entire perimeter of the body and is separated from all other segmented second contacts by portions of the body or the alignment slit; and
    a plurality of conductors electrically coupling the plurality of first contacts to the plurality of second contacts.

2. The electrical stimulation lead or lead extension of claim 1, wherein the segmented second contacts are arranged in a plurality of sets of segmented second contacts, wherein each set of segmented second contacts comprises at least two of the segmented second contacts disposed in a circumferential arrangement at a same longitudinal position of the lead.

3. The electrical stimulation lead or lead extension of claim 2, wherein the alignment slit extends between at least two of the segmented second contacts of each of the sets of segmented second contacts.

4. The electrical stimulation lead or lead extension of claim 2, wherein each of the sets of segmented second contacts contains exactly two segmented second contacts.

5. The electrical stimulation lead or lead extension of claim 1, wherein, each of the two sections further defines a bendable portion distal to all of the segmented second contacts, wherein the bendable portions of the two sections allow the sections to be sufficiently separated so that the sections can be inserted into different connectors.

6. The electrical stimulation lead or lead extension of claim 1, wherein the first contacts are electrodes and the segmented second contacts are segmented terminals and the electrical stimulation lead or lead extension is an electrical stimulation lead.

7. The electrical stimulation lead or lead extension of claim 1, wherein the first contacts are connector contacts and the segmented second contacts are segmented terminals and the electrical stimulation lead or lead extension is a lead extension.

8. An electrical stimulation system comprising:
    the electrical stimulation lead or lead extension of claim 1; and
    a first connector defining a connector lumen configured and arranged to receive at least a portion of the proximal end of the body of the electrical stimulation lead or lead extension, wherein the first connector comprises a plurality of segmented connector contacts disposed along the connector lumen.

9. The electrical stimulation system of claim 8, further comprising a control module, wherein the control module comprises the connector, a housing, and an electrical subassembly disposed in the housing and electrically coupled to the connector contacts of the connector.

10. The electrical stimulation system of claim 8, further comprising a lead extension, wherein the lead extension comprises the connector.

11. The electrical stimulation system of claim 8, wherein the connector contacts of the first connector are arranged in a plurality of sets of segmented connector contacts, wherein each set of segmented connector contacts comprises at least two of the segmented connector contacts disposed in a circumferential arrangement at a same longitudinal position along the connector lumen.

12. The electrical stimulation system of claim 8, wherein the connector further comprises a connector housing containing the connector lumen and defining an opening into the connector lumen, and
an alignment structure extending across the connector lumen and configured and arranged to mate with the alignment slit of the body of the electrical stimulation lead or lead extension.

13. The electrical stimulation system of claim 8, further comprising a second connector defining a connector lumen configured and arranged to receive the proximal end of the body of the electrical stimulation lead or lead extension, wherein the second connector comprises a plurality of segmented connector contacts disposed along the connector lumen,
wherein the electrical stimulation lead or lead extension is configured and arranged so that the alignment slit separates the proximal portion of the body into a first branch and a second branch, wherein each of the first and second branched further defines a bendable portion distal to all of the segmented second contacts, wherein the bendable portions of the first and second branches allow the first and second branches to be sufficiently separated so that the first and second branches can be separately inserted into the first and second connectors, respectively.

14. An electrical stimulation lead or lead extension, comprising:
a body having an outer surface, a proximal end, a cylindrical proximal portion, at least one distal portion, a perimeter, and a longitudinal length, the body defining an alignment slit extending distally from the proximal end of the body and splitting the proximal portion of the body into two transversely spaced apart, non-cylindrical arc sections;
a plurality of first contacts disposed along the at least one distal portion of the body;
a plurality of non-cylindrical segmented second contacts disposed along the proximal portion of the body, wherein each segmented second contact extends around less than the entire perimeter of the body a is separated from all other segmented second contacts by portions of the body or the alignment slit;
a plurality of conductors electrically coupling the plurality of first contacts to the plurality of second contacts; and
a retention sleeve disposed distal of all of the segmented second contacts.

15. The electrical stimulation lead or lead extension of claim 14, wherein the alignment slit separates the retention sleeve into two laterally spaced-apart pieces.

16. The electrical stimulation lead or lead extension of claim 14, wherein the alignment slit terminates proximal to the retention sleeve.

17. An electrical stimulation system comprising:
the electrical stimulation lead or lead extension of claim 14; and
a first connector defining a connector lumen configured and arranged to receive at least a portion of the proximal end of the body of the electrical stimulation lead or lead extension, wherein the first connector comprises a plurality of segmented connector contacts disposed along the connector lumen.

18. The electrical stimulation system of claim 17, further comprising a control module, wherein the control module comprises the connector, a housing, and an electrical subassembly disposed in the housing and electrical coupled to the connector contacts of the connector.

19. The electrical stimulation system of claim 17, further comprising a lead extension, wherein the lead extension comprises the connector.

20. The electrical stimulation lead or lead extension of claim 14, wherein the first contacts are electrodes and the segmented second contacts are segmented terminals and the electrical stimulation lead or lead extension is an electrical stimulation lead.

* * * * *